US012697125B2

(12) United States Patent
Addis

(10) Patent No.: US 12,697,125 B2
(45) Date of Patent: Aug. 4, 2026

(54) TOROIDAL OCCLUSION AND MOLDING BALLOONS AND METHODS OF USE

(71) Applicant: Bruce Addis, Redwood City, CA (US)

(72) Inventor: Bruce Addis, Redwood City, CA (US)

( * ) Notice: Subject to any disclaimer, the term of this patent is extended or adjusted under 35 U.S.C. 154(b) by 502 days.

(21) Appl. No.: 18/241,582

(22) Filed: Sep. 1, 2023

(65) Prior Publication Data

US 2024/0074764 A1 Mar. 7, 2024

Related U.S. Application Data

(60) Provisional application No. 63/403,653, filed on Sep. 2, 2022.

(51) Int. Cl.
*A61B 17/12* (2006.01)
(52) U.S. Cl.
CPC .. *A61B 17/12136* (2013.01); *A61B 17/12109* (2013.01)
(58) Field of Classification Search
CPC ........ A61B 17/12136; A61B 17/12036; A61B 17/12; A61M 25/10
See application file for complete search history.

(56) References Cited

U.S. PATENT DOCUMENTS 6,607,546 B1 * 8/2003 Murken ........... A61B 17/12104
606/198
8,460,240 B2 6/2013 Towler 2001/0039450 A1 * 11/2001 Pavcnik .................... A61F 2/01
623/1.36
2002/0115982 A1 * 8/2002 Barbut ................. A61B 5/0215
604/509
2004/0158276 A1 * 8/2004 Barbut ............. A61B 17/12109
606/200
2006/0052803 A1 * 3/2006 Maginot .......... A61B 17/12045
606/153

FOREIGN PATENT DOCUMENTS

WO WO-9852476 A1 * 11/1998 ....... A61B 17/12109

* cited by examiner

*Primary Examiner* — Katherine H Schwiker
*Assistant Examiner* — Zehra Jaffri
(74) *Attorney, Agent, or Firm* — Acuity IP, LLC; Nathan S. Cassell

(57) ABSTRACT

Exemplary occlusion and molding devices and methods involve the use of an expandable balloon. Methods of sealing an aortic side branch in a patient can include advancing an occlusion device within the aorta, positioning a toroidal balloon of the occlusion device adjacent to the aortic side branch, and inflating the balloon to prevent peripheral blood flow from the aorta into the aortic side branch while a central aperture of the balloon allows descending aortic blood flow therethrough. Methods of molding a stent against an interior surface of a vessel of a patient can include advancing a molding device within the vessel, positioning a toroidal balloon of the molding device at least partially withing the stent, and inflating the balloon to exert force to the stent thus dilating the stent and molding it to the interior of the vessel while a central aperture of the balloon allows blood flow therethrough.

16 Claims, 17 Drawing Sheets

BULK

OFFSET REDUCES STOWED BULK

132A

134A 136A  136A 138A       138B       138C

TOROIDAL OCCLUSION AND MOLDING BALLOONS AND METHODS OF USE

CROSS-REFERENCES TO RELATED APPLICATIONS

This application claims the benefit of U.S. Provisional Patent Application No. 63/403,653 filed Sep. 2, 2022, the content of which is incorporated herein by reference.

BACKGROUND

In medical vascular procedures, occlusion with balloons is an accepted standard practice to create hemostasis (stopping blood flow as during surgery). A typical surgery where this might be used is spleen removal or a splenectomy. Removal of the spleen can be necessitated from trauma causing internal injuries, or oncology treatments which overload the organ such as chemotherapy which breaks down certain tissues at a rate higher than the spleen can accommodate removal. To perform this surgery, the blood flow to the spleen is sealed shut while the surgeon removes or modifies the spleen. The spleen is an organ which receives significant blood flow, and losing control of hemostasis can result in large blood loss and death. The splenic artery is the vessel which connects the spleen to the aorta experiences pulsatile systolic and diastolic blood pressure. Normal blood pressure being approximately 120 over 70 mm Hg (2.3 over 1.4 psi) although these numbers can be much higher in a patient suffering from high blood pressure (hypertensive). The splenic artery is occluded by occluding the aorta at the splenic artery takeoff, the location in which the splenic artery joins with the aorta.

An occlusion balloon can be used to occlude the aorta. The occlusion balloon is pressurized beyond blood pressure to stop blood flow creating a seal against the aortic wall, and significantly more to stop migration (sliding) in aorta due to pulsatile blood pressure. Spherical shaped occlusion balloons are either compliant or non-compliant balloons which come in a variety of sizes to accommodate different diameter vessels. Non-compliant balloons take on a set shape with a relatively fixed diameter. They are very strong and made from materials (e.g. polyethylene terephthalate (PET)) which can safely sustain pressures seen in carbonated soda bottles of approximately 160 psi or 8,300 mm Hg which is approximately 70 times the mean pressure in the aorta, and can be used in aortic balloons at pressures of approximately 65 psi which is approximately 26 times higher than blood pressure. This can create stresses, damaging the aorta. Increasing pressure in spherical shaped occlusion balloons once inflated results in a very small dimensional increase which further takes away any sense for the stress being applied to the aorta when hundreds of pounds of pressure are being adjusted in a vessel which only carries approximately 1 to 2.5 pounds of pressure per square inch. Thus, safe hemostasis relies on the skill of the physician balancing the inflation pressure with the necessary pressure that will achieve hemostasis and not cause harm. A compliant balloon made with materials that are elastic naturally take on a spherical shape as they are inflated. These balloons will grow in size uniformly with pressure. The spherical shaped balloon is over-inflated as necessary to fix its position in the aorta to hold back the full pulsatile pressure of the heart. The balloon is significantly over-inflated as the spherical balloon holds back the full flow and pressure from the heart. The balloon operates by anchoring or fixation against the smooth and lubricious aorta walls with flowing blood. The pressures involved, and easily obtainable with such balloons can achieve pressures many times greater than the anatomy would ever experience, and damage to the aorta with subsequent hemorrhage and resulting death is an incipient and precariously balanced risk.

When using conventional occlusion balloons, the inflation pressure can easily go beyond the physical tensile limitations of the aorta causing aortic dissection, which is the tearing open of the largest blood carrying conduit in the body coming directly from the heart causing severe internal bleeding (hemorrhage) and death. Such high inflation pressure can also cause separation of the vessel's lamina creating a false lumen or aortic dissection, which can involve a flap of the internal aortic lining that will close off the aorta and re-direct the blood pressure within the wall of the aorta propagating axially through the wall either re-directing into the aorta, or outside the aorta causing hemorrhage and death, or other associated trauma. All of the aforementioned are very serious life-threatening conditions requiring surgical intervention with possible fatal results. Devices and methods which provide hemostasis while reducing or eliminating the risk of over pressurization are desired. At least some of these objectives are met by embodiments of the present invention.

SUMMARY

Embodiments of the present invention generally relate to medical systems, devices and methods, and more particularly relate to minimally invasive surgical techniques or vascular catheterization which can control or modulate the flow of blood through a vessel. In some embodiments, the systems, devices, and methods disclosed herein can be used to replace existing approaches which often require the use of a cross-clamp.

In some embodiments, a device is provided having a toroidal compliant balloon which will conform to the interior walls of a blood vessel, such as the aorta, so as to occlude one or more target side branches with minimum or low pressure while maintaining blood flow through the main blood vessel. The pressure provided is that which will inflate the balloon to obstruct the opening in the aortic wall to the aforementioned side branch artery (ostium), with only a minimal further inflation pressure if any to halt migration, and to keep the tethered toroidal balloon confidently positioned in the aorta at the desired level. This pressure is relatively low as blood flow down the aorta is unobstructed flowing freely through the center of the balloon toroid's axis. In certain embodiments, pressure is provided to the balloon via one or more tether elements which are in fluid communication with the balloon.

The balloon design being compliant conforms to the anatomy of the vessel with very low pressure. The low pressure being enough to expand the balloon into the directed vessel sites to assure occlusion, but not over distend the aorta causing trauma such as dissection, false lumen, or rupture.

The catheter portion of the device is small enough such that it can be inserted through a typical femoral cannulation site and be steered under fluoroscopic guidance to the target site where occlusion is needed. The device may have a guidewire lumen integral to the device used as part of the actuation mechanism which will allow typical guidewires used in catheter procedures being approximately 0.014-0.035" diameter with a floppy atraumatic "J" tip. The balloon may be filled and inflated with a contrast media that will show under fluoroscopy. Further, the device may have radiopaque markers as necessary to guide the effective device placement. The device can have a handle with a Luer fill port of a standard convention used to transfer the liquid contrast balloon fill media.

The toroidal balloon can be used to post dilate a stent graft so that after installation of the stent graft, portions of the stent graft which the physician feels need post dilation can be dilated while maintaining axial blood flow. This operation can use a semi-compliant balloon which can enable effective control of the diameter of the balloon, and in doing so, can have greater positioning accuracy while also not stopping the flow of blood through the vessel.

In a first aspect, embodiments of the present invention encompass systems and methods involving a compliant occlusion balloon having a toroidal geometry which provides a relatively large bore for blood flow along major axis. In some cases, a side surface or cap of a toroidal compliant balloon can expand to cover aortic side branches providing occlusion thereof. In some cases, a compliant balloon has tether attachment points located in two orthogonal planes with planes intersecting along toroid major axis. One, or a plurality of the tethers can contain lumens which will provide fluid communication for liquid contrast media, saline, or other suitable liquid to expand compliant balloon. In some cases, tethers can fill and evacuate a compliant toroidal balloon, and support and stabilize a toroidal balloon so that side sealing surfaces are orthogonal to major axis.

In another aspect, embodiments of the present invention encompass systems having a catheter or shaft portion that provides a support chassis for the compliant toroidal balloon, and one or more of its operational elements. In some cases, a support shaft or catheter can be made from smooth biocompatible materials which can be saline flushed before use. A support shaft or catheter can have a manipulator on the proximal end containing the mechanism to deploy and stow the device. Standard Luer fittings can be used for one or more all fluid connections of a device or system. A support shaft or catheter can have a section which the compliant toroidal balloon can be stowed in, and deployed from.

In still another aspect, embodiments of the present invention encompass methods for making a compliant or semi-compliant toroidal balloon with a major axis aligned with a support shaft or catheter with tethered connections. In some cases, the tethers can be in pairs positioned in orthogonal planes on opposite sides of the compliant toroidal balloon axis. Exemplary embodiments also encompass methods whereby the tethered compliant toroidal balloon has tethers which provide fluid communication for filling and evacuating the balloon.

In another aspect, embodiments of the present invention encompass methods for selecting an aortic side branch prior to the tethered compliant balloon being deployed for the purpose of compromising the seal to profuse the selected organ.

In another aspect, embodiments of the present invention encompass the use of a support shaft or catheter portion which attaches to the tethered compliant toroidal balloon having axially sliding catheter attach points being able to move the controlling and or inflation tethers grouped in orthogonal planes in opposing directions to facilitate the folding and stowage of the balloon.

In yet another aspect, embodiments of the present invention encompass a device having a balloon and tethers, where the tethers are symmetrically in two elongated sections such that the bulk and crossing profile of the balloon is minimized, allowing the balloon to be passed through a small passage when the device is advanced into or retracted from the patient's body.

In another aspect, embodiments of the present invention encompass devices which include inflation tethers having an internal surface geometry feature that prevent the tethers from collapsing when suction is applied. The internal surface geometry feature can be one or more raised helical spines. The internal surface geometry feature can also be one or more raised bumps. The internal surface geometry feature can include splined beading. A spline can have one or more lobes which are prismatic or round in cross-section. Beading can include a loose braid or a twisted string.

In one aspect, embodiments of the present invention encompass systems and methods that involve staggering of the tethers on balloon retraction which orients the bulk distribution reducing the crossing profile. In some cases, a support shaft or catheter can have a mechanism that pulls on one of the proximal tethers (leading tethers when retracting) to offset the balloon bulk.

In some cases, a toroidal balloon can be a semi-compliant balloon or a non-compliant balloon for stent dilation without obstructing or holding back blood flow through a portion of the vasculature in which the balloon is placed.

In yet a further aspect, embodiments of the present invention encompass methods for sealing an aortic side branch in an aorta of a patient using an occlusion device. Exemplary methods include advancing the occlusion device within the aorta of the patient, where the occlusion device has a toroidal balloon, positioning the toroidal balloon of the occlusion device adjacent to the aortic side branch of the patient, and inflating the toroidal balloon so that a side surface of the toroidal balloon prevents peripheral blood flow from the aorta into the aortic side branch while a central aperture of the toroidal balloon allows descending aortic blood flow therethrough. In some cases, the aortic side branch can be a mesenteric artery side branch, a renal artery side branch, a gonadal artery side branch, a celiac artery side branch, or an intercostal artery side branch. In some cases, the aortic side branch is located in a descending portion of the aorta of the patient. In some cases, the aortic side branch is located in an abdominal portion of the aorta of the patient. In some cases, the occlusion device includes a proximal tether assembly coupled with the toroidal balloon, and the step of inflating the toroidal balloon includes delivering fluid through the proximal tether assembly into the toroidal balloon. In some cases, the occlusion device includes a distal tether assembly coupled with the toroidal balloon, and the step of inflating the toroidal balloon includes delivering fluid in a proximal direction through the distal tether assembly into the toroidal balloon. In some cases, the occlusion device includes a manifold cap coupled with the distal tether assembly, and the step of inflating the toroidal balloon includes delivering fluid through the manifold cap into the distal tether assembly. In some cases, the occlusion device includes a support shaft coupled with the cap, and the step of inflating the toroidal balloon includes delivering fluid in a distal direction through the support shaft into the manifold cap. In some cases, the occlusion device includes a guidewire, and the step of advancing the occlusion device within the aorta of the patient includes advancing the toroidal balloon along the guidewire. In some cases, the occlusion device includes an elongate shaft, a proximal tether assembly having a first proximal tether and a second proximal tether, and a distal tether assembly having a first distal tether and a second distal tether. In some cases, the first proximal tether is attached with the toroidal balloon at a first proximal attachment point and the second proximal tether is attached with the toroidal balloon at a second proximal attachment point opposite the first proximal attachment point. In some cases, the first distal tether is attached with the toroidal balloon at a first distal attachment point and the second distal tether is attached with the toroidal balloon at a second distal attachment point opposite the first distal attachment point. In some cases, a method includes drawing the first distal attachment point and the second distal attachment point in a distal direction using the distal tether assembly or drawing the first proximal attachment point and the second proximal attachment point in a proximal direction using the proximal tether assembly so as to produce a four eared ring configuration in the toroidal balloon, and positioning the toroidal balloon within the elongate shaft when the toroidal balloon is in the four eared ring configuration.

In another aspect, embodiments of the present invention encompass occlusion devices for sealing an aortic side branch in an aorta of a patient. Exemplary occlusion devices can include a toroidal balloon having a proximal surface and a distal surface, a proximal tether assembly coupled with the proximal surface of the toroidal balloon and a distal tether assembly coupled with the distal surface of the toroidal balloon, an elongate shaft configured to store the toroidal balloon when the toroidal balloon is in an uninflated state, a support shaft configured to move within the elongate shaft, and a cap coupled with the support shaft and the distal tether assembly. In some cases, the proximal tether assembly is configured to deliver fluid to the toroidal balloon. In some cases, the distal tether assembly is configured to deliver fluid to the toroidal balloon. In some cases, the cap is a manifold cap and is configured to receive fluid from the proximal support shaft and direct fluid to the distal tether assembly. In some cases, an occlusion device includes a guidewire configured to move within the support shaft. In some cases, the proximal tether assembly includes a first proximal tether and a second proximal tether, and the distal tether assembly includes a first distal tether and a second distal tether. In some cases, the first proximal tether is attached with the toroidal balloon at a first proximal attachment point and the second proximal tether is attached with the toroidal balloon at a second proximal attachment point diametrically opposed to the first proximal attachment point. In some cases, the first distal tether is attached with the toroidal balloon at a first distal attachment point and the second distal tether is attached with the toroidal balloon at a second distal attachment point diametrically opposed to the first distal attachment point. In some cases, the toroidal balloon is configured to assume a four eared ring configuration when the proximal tether assembly draws the first proximal attachment point and the second proximal attachment point in a proximal direction or when the distal tether assembly draws the first distal attachment point and the second distal attachment point in a distal direction. In some cases, relative positions of the first proximal attachment point, second proximal attachment point, first distal attachment point, and second distal attachment point are staggered along a length of the elongate shaft when the toroidal balloon is in the uninflated state and stored in the elongate shaft, thus enabling a reduced crossing profile for the toroidal balloon. In some cases, the distal tether assembly includes a first distal tether having a distal internal surface geometry feature that prevents the first distal tether from collapsing when suction is applied thereto, and/or the proximal tether assembly includes a first proximal tether having a proximal internal surface geometry feature that prevents the first proximal tether from collapsing when suction is applied thereto. In some cases, the toroidal balloon is a compliant toroidal balloon, a semi-compliant toroidal balloon, or a non-compliant toroidal balloon.

In another aspect, embodiments of the present invention encompass methods for molding a stent against an interior surface of a vessel of a patient using a molding device. Exemplary methods include advancing the molding device within the vessel of the patient, where the molding device has a toroidal balloon, positioning the toroidal balloon of the molding device at least partially withing the stent, and inflating the toroidal balloon so that the toroidal balloon exerts a external circumferential expanding force to the stent thus dilating the stent and molding the stent to the interior surface of the vessel while a central aperture of the toroidal balloon allows blood flow therethrough.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Specific embodiments of the disclosed device, delivery system, and method will now be described with reference to the drawings. Nothing in this detailed description is intended to imply that any particular component, feature, or step is essential to the invention.

Figure 1A:
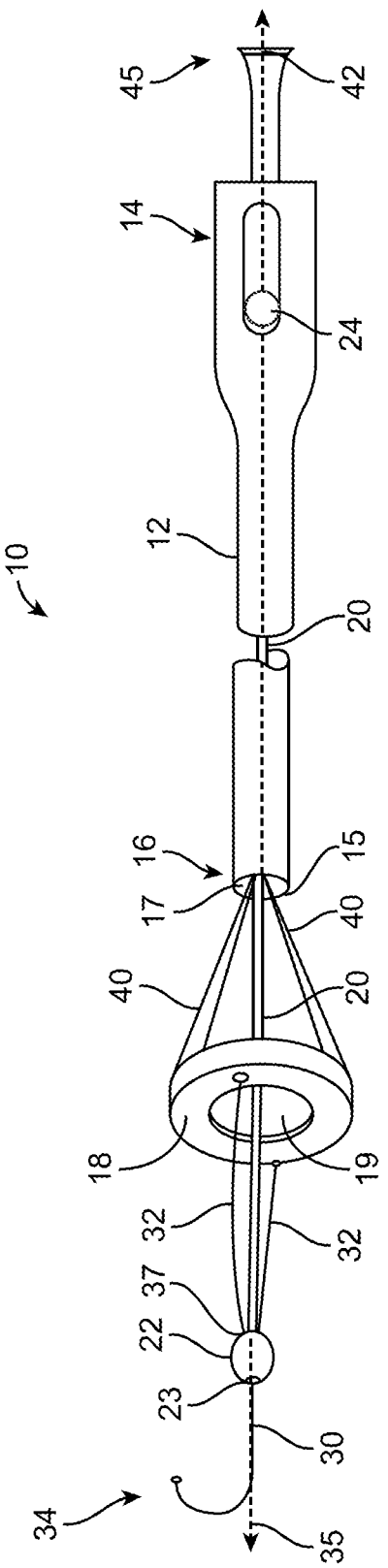
FIG. 1A is an isometric view showing an embodiment of the device with the toroidal balloon deployed. The balloon may be compliant, semi-compliant, or non-compliant.

FIG. 1A illustrates an embodiment of a vascular catheter device 10 in a deployed configuration according to the present invention. The device 10, which may also be referred to as a toroidal occlusion balloon system or device, comprises an elongate shaft 12 having a proximal end 14 and a distal end 16, wherein the distal end 16 is connected with or in operative association with a toroidal balloon 18. The toroidal balloon 18 is collapsible and insertable within the distal end 16 for delivery. For example, the balloon 18 may be stowed within or extended distally from an interior lumen 17 of the distal end 16 of the elongate shaft 12. The device 10 is configured to be advanced into a vessel of a body of a patient where the toroidal balloon 18 is deployed during use, as described elsewhere herein. In some embodiments, the shaft 12 is approximately 30 to 50 cm long with the largest (outer) diameter having a value within a range from 9 to 18 French (3 to 6 mm), and in some cases having a value within a range from 9 to 10 French.

In this embodiment, a support shaft 20 is provided which extends through the elongate shaft 12, through a central opening 19 in or defined by the toroidal balloon 18 and is fixedly attached to an olive or cap 22. The cap 22 can include or be manufactured from polycarbonate, polyethylene terephthalate (PET), acrylonitrile butadiene styrene (ABS), polyurethane, or similar suitable material and serves as an atraumatic cap for the device 10. Thus, the cap 22 provides a smooth distal fairing capturing the edge of the catheter device 10 when the compliant toroidal balloon 18 is stowed for ingress and/or egress through the cannulation and vasculature. For example, the cap 22 can cover the rim or edge 15 of the distal end 16 of the shaft 12. In some embodiments, the (outer) diameter of the cap 22 can be approximately the same as the (outer) diameter of the shaft 12 (or the distal end 16 thereof), such as 3 to 6 mm in diameter, and the cap 22 can have a length of approximately 5 to 25 mm with a slightly curved "barrel" shape to facilitate the balloon stowing and transition to the catheter distal opening. For example, the cap 22 can have a convex shape with a bulge at the center. In some embodiments, the cap 22 can operate as a hub pulling on the stowed toroidal balloon 18 during deployment when acted upon by the support shaft 20. For example, the support shaft 20 can be advanced distally, and by virtue of a connection between the shaft 20 and the cap 22, and a connection between the cap 22 and the balloon 18 (e.g. via tethers 32), distal advancement of the shaft 20 can result in distal advancement of the balloon 18. In some embodiments, the cap 22 can be provided as a manifold cap. In some cases, the cap 22 can be provided as a trunnion cap. In some embodiments, a shaft 12 is optional, and hence the device 10 may or may not include a shaft 12.

In the embodiment depicted in FIG. 1A, the support shaft 20 is advanced and retracted by a manipulator 24, and is connected through the entire device to the cap 22. For example, the support shaft 20 can extend through the elongate shaft 12. The manipulator 24 can be coupled with or in operative association with the shaft 20. The support shaft 20 can provide a channel or lumen for a guidewire 30 to be introduced there through. For example, as shown in the cross-section view of FIG. 1B, support shaft 20 can have or include a central lumen 21 and the guidewire 30 can be positioned within the lumen 21. In some embodiments, the guidewire 30 is advanced from the proximal end 14 to the most distal component being the cap 22. The guidewire 30 also runs through the entire device 10 with egress from the cap 22. As such, the cap 22 may have a central lumen 23 passing therethrough, which allows positioning of the guidewire 30 within the cap 22. Such guidewires 30 typically have (outer) diameters of approximately 0.014 to 0.035 inches, and are comprised of or include wire designed to have varying degrees of stiffness. In some embodiments, the guidewire 30 has a "J" shape at its distal end 34, the guidewire 30 being most flexible at the distal "J" end so as to be atraumatic. The guidewire 30 can also be used for device placement using a traditional Seldinger technique of placing the guidewire 30 in place, then advancing the entire device 10 to a target site within the body before deploying the tethered compliant toroidal balloon 18. In some cases, the guidewire 30 extends all the way through the cap 22, for example through a lumen 23 of the cap or a coaxial tube within the cap. In some cases, the guidewire 30 is fixed on the cap and extends distally therefrom. In some cases, the shaft 20 can have multiple lumens, for example one or more lumens which provide fluid to and/or from one or more of the tethers, and one or more lumens which provide a passageway for other types of elements such as guidewires. In some embodiments, guidewire 30 can enable use of the device 10 in an over the wire (OTW) fashion.

In this embodiment, the toroidal balloon 18 is connected with the cap 22 by tethers 32. FIG. 1A illustrates two tethers 32, however it may be appreciated that one, two, three, four, and five or up to twelve or more tethers 32 may be present. These distal tethers 32 may be comprised of or include straps having a cross-section with a height and a width, where the height can have a value within a range from about 0.1 mm to about 0.4 mm and the width can have a value within a range from about 2 mm to about 10 mm Typical distal tethers 32 are made from polymers accepted in the medical device fields such as Pebax® or other thermoplastic elastomers (TPE), nylon or other synthetic polymers, Kevlar® or other fibers, polyphenylene ether (PPE), high density polyethylene (HDPE), low density polyethylene (LDPE), polyvinylidene fluoride (PVDF), polyimide (PI), polyethylene terephthalate (PET), polyurethane, Tecothane®, PEEK, PI, PA, and the like. The length of these distal tethers 32 can be long enough to allow the compliant toroidal balloon 18 to maintain its primary axis aligned with a longitudinal axis 35 of the device 10, but short enough to minimize bulk and cross section when the balloon 18 is stowed. Typical dimensions for the distal tethers 32 can be approximately 50 mm in length and in some embodiments can have a length within a range from 10 to 100 mm.

In some embodiments, the tethers 32 can be provided as lumens or tubes, and the cap 22 can operate as a manifold. In this sense, fluid can be provided to the balloon 18 via one or more tethers 32, which in turn receive fluid via the cap 22, which in turn can receive fluid from the shaft 20. With regard to fluid flow in the opposite direction (e.g. for inflation/deflation), fluid may flow from balloon 18 through one or more tethers 32 to the cap 22, and from the cap 22 into the shaft 20. Additional aspects of the manifold feature are discussed elsewhere herein, for example in reference to FIG. 9. Tethers 32 can be coupled with cap 20, for example via fixed connections 37.

Figure 1C:
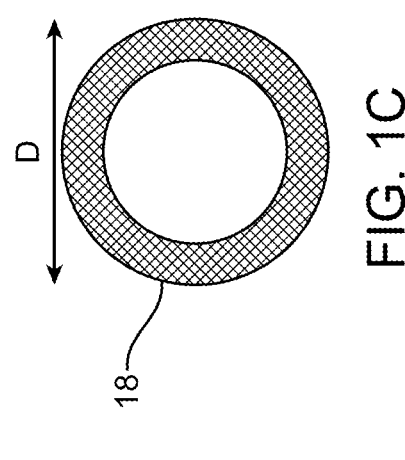
FIGS. 1B to 1D depict aspects of a toroidal balloon device, according to embodiments of the present invention.
Figure 1B:
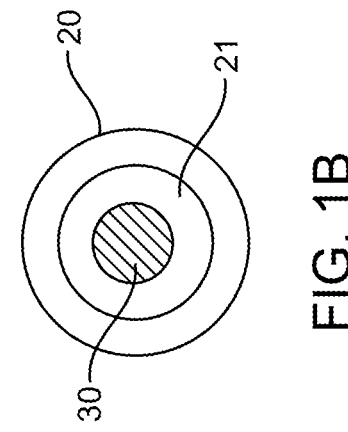

In some embodiments, the tethered compliant toroidal balloon 18, when just inflated to its formed state, is approximately 19 mm in diameter about its main axis, with a cross-sectional diameter D of approximately 7 mm, as depicted in FIG. 1C. When the compliant tethered toroidal balloon 18 is inflated beyond its formed dimensions, the outermost diameter can expand to seal against the vessel wall, such as an aortic wall, reaching approximately 60 mm Typically, the balloon 18 is comprised of or includes a material of accepted biocompatibility properties found in medical devices with elongation properties of approximately 100 to 400% elongation, such as silicone, polyurethane, latex, or guayule.

The toroidal balloon 18 can be connected to one or a plurality of inflation tethers 40. In some embodiments, each inflation tether 40 has and/or is in fluid communication with a lumen for delivering inflation liquid, such as saline and/or contrast media, to the balloon 18. Each lumen can run the length of the catheter shaft 12 (or at least a portion thereof) to a connector such as a standard medical Luer connector 45. The Luer connector 45 can operate as a port for fluid communication to fill/deflate the balloon 18 via the inflation tether(s) 40 and/or the tethers 32. Fluid flow through the Luer connector 45 can be modulated or controlled using a Luer lock 42 or valve. In some embodiments, the inflation tethers 32, 40 are comprised of or include materials such as polyurethane, Pellethane®, Tecothane®, C-Flex®, polyimide, polyether ether ketone (PEEK), and silicone. In some embodiments, the length of each inflation tether 40 is long enough to allow the compliant toroidal balloon 18 to maintain its primary axis aligned with the catheter axis 35, but short enough to minimize bulk and cross section when stowed. Typical dimensions for the inflation tethers 40 are approximately 50 mm in length, and in some embodiments can range from 10 to 100 mm with a lumen of approximately 0.25 to 0.75 mm with a thin wall of approximately 0.04 to 0.5 mm. These provide the fluid coupling to the toroidal compliant, non-compliant, or semi-compliant balloon 18. In some cases, one or more tethers 32 can also provide fluid to and receive fluid from the balloon 18. In this sense, one or more tethers 32 and/or tethers 40 can operate as inflation ports and/or deflation ports. In some cases, the balloon 18 is in fluid communication with only one or more tethers 32. In some cases, the balloon 18 is in fluid communication with only one or more tethers 40.

In the embodiment depicted in FIG. 1A, the compliant toroidal balloon 18 is not mounted on the elongated shaft 12 so as to allow control of the balloon 18 without constraint as the balloon expands. This also allows for the elongated shaft 12 to remain mostly concentric within the central axis of the compliant toroidal balloon 18 at any level of inflation. The position of the balloon 18 can be controlled by the two distal inflation tethers 32, and two proximal inflation tethers 40. In some embodiments, the tethers 32, 40 can be of equal length to help assure symmetry, and uniform control of the balloon 18 when deployed and as it expands.

Figure 1D:
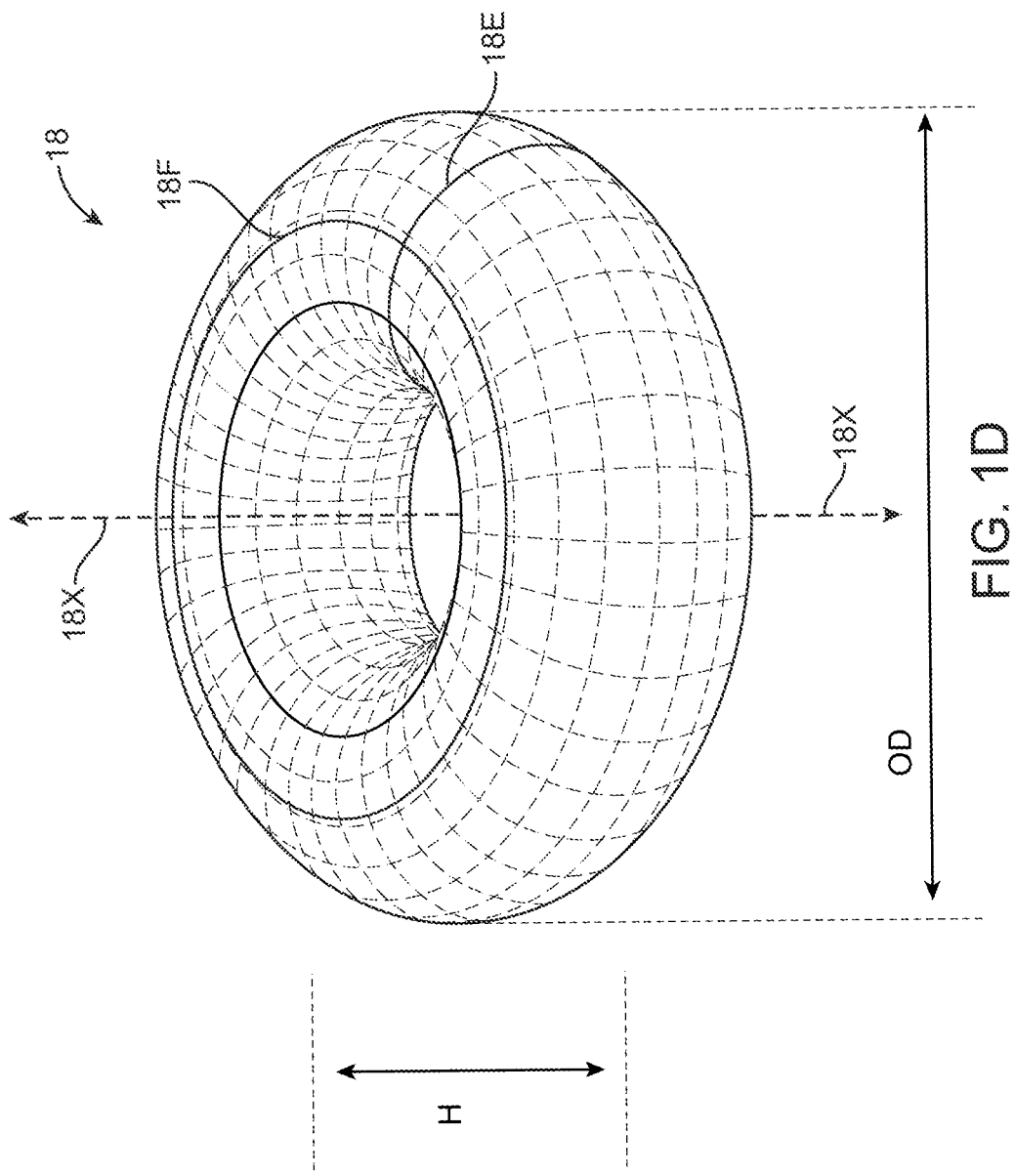

FIG. 1D depicts aspects of an exemplary balloon 18. As shown here, the balloon 18 can have a primary or central axis 18X. The shape or outer surface of the balloon 18 can be defined by a first shape 18E (e.g. circle) that is swept around axis 18X which also can be defined by second shape (e.g. circle). As shown here, the balloon has an upper or distal surface that can be defined by circle 18F. Where first shape 18E is a circle, the balloon can have a height H that is equal to the diameter of 18E. The balloon can have a height H that is defined by the height of first shape 18E, and when first shape 18E is a circle, the balloon can have a height that is defined by the diameter of the circle. In some embodiments, the first shape 18E can be a circle having a diameter value within a range from about 4 mm to about 20 mm. In some embodiments, the outer diameter OD of the balloon can have a value within a range from about 10 mm to about 65 mm. In some embodiments, first shape 18E can have a non-circular shape, for example an oval or ellipsoid.

Figure 2A:
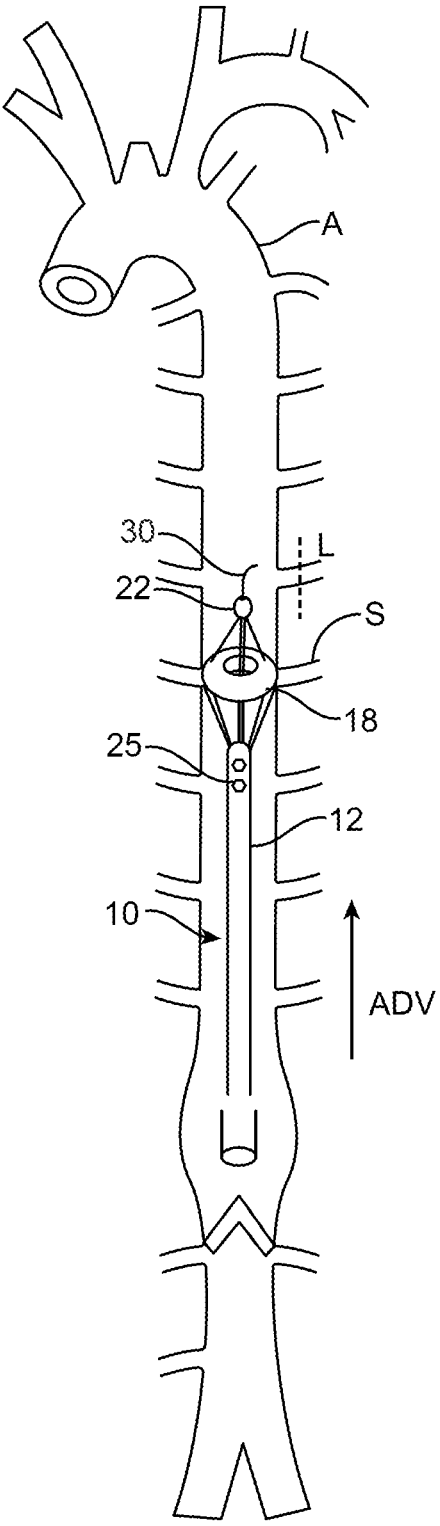
FIG. 2A is an anatomical view of the major portion of the descending aorta with its plurality of side branch pairs and an embodiment of the device positioned therein.

As mentioned, the device 10 can be used to occlude side branches of a blood vessel while maintaining blood flow through the blood vessel to locations downstream. In particular, the device 10 may be used in an aorta A of a patient, such as illustrated in FIG. 2A, so as to occlude at least one side branch S. In this way, a device 10 having a toroidal compliant balloon 18 can conform to the interior walls of a blood vessel, such as the aorta, so as to occlude one or more target side branches with minimum or low pressure while maintaining blood flow through the main blood vessel (e.g. aorta A) as blood continues to travel down the aorta in an unobstructed manner, via a flow path that goes through the center of the balloon toroid's axis. In this way, the device 10 can be used to replace existing solutions which may require the use of a cross-clamp. For example, some existing approaches involve the use of a surgical steel clamp placed across a side branch (e.g. location L) to seal the side branch artery. Balloon embodiments of the present invention provide a less traumatic technique for sealing or controlling flow to the side branch. In some embodiments of the present invention, a physician can introduce the guidewire 30 through a typical femoral cannulation accessed in the femoral artery by means of a Seldinger technique or variation thereof. The guidewire 30 can be positioned using cine X-ray (fluoroscopy). The device 10 can then be advanced over the guidewire 30, wherein the balloon 18 is stowed within the device 10. When the balloon 18 is deployed, the side of the balloon nestles against the side branch ostium, and can slightly protrude into the side branch vessel itself, creating a seal that prevents flow into the side branch vessel. In some embodiments, the cap 22 can be provided as a manifold cap. In some cases, the cap 22 can be provided as a trunnion cap.

Figure 2B:
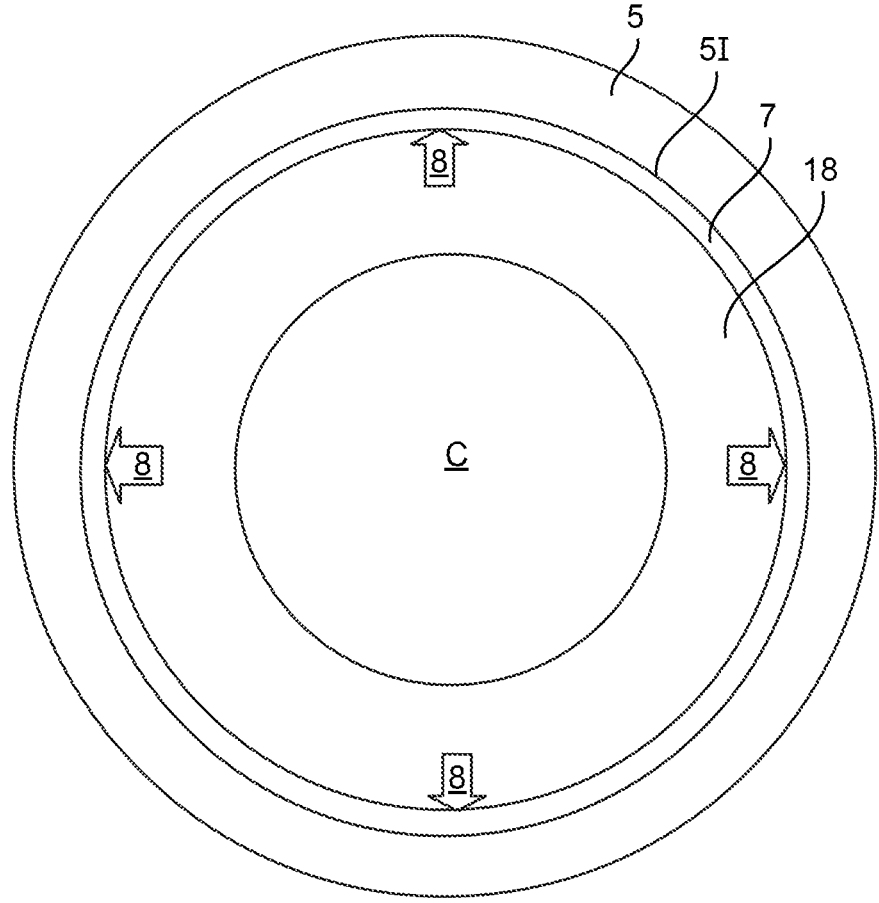
FIG. 2B depicts aspects of a molding balloon, according to embodiments of the present invention.

FIG. 2B provides a cross-section view of a blood vessel or lumen 5 of a patient, a stent 7 positioned within the blood vessel or lumen 5, and a balloon 18 positioned interior to the stent 7. When the balloon 18 is inflated, it applies an external circumferential expanding force 8 to the stent 7, thus dilating the stent 7 and/or molding the stent 7 to the interior surface SI of the blood vessel or lumen 5. In this way, a toroidal balloon can be used to post dilate a stent or stent graft so that after installation of the stent or stent graft, portions of the stent or stent graft which the physician feels need post dilation can be dilated while maintaining axial blood flow through a central aperture C of the balloon 18 and therefore through the blood vessel or lumen 5 as well. This operation can use a semi-compliant balloon which can enable effective control of the diameter of the balloon, and in doing so, can have excellent positioning accuracy while also not dealing with force from stopping the flow of blood through the vessel.

Figure 3A:
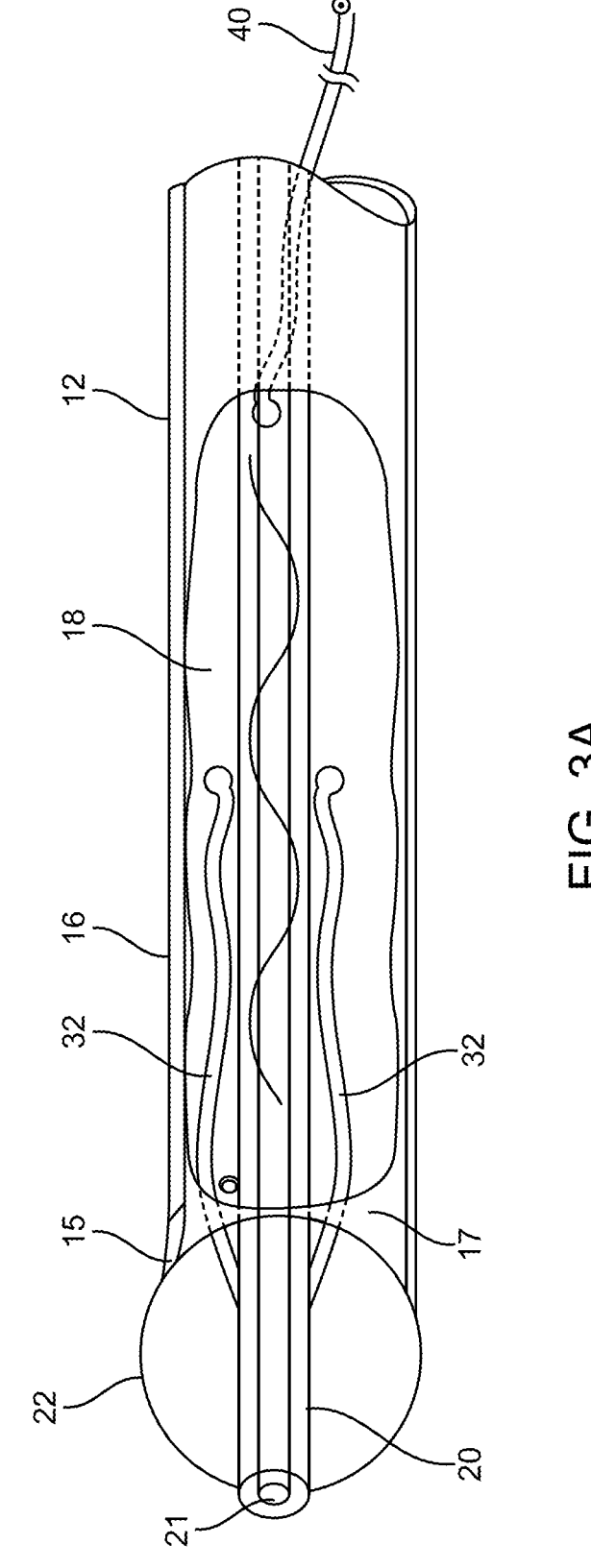
FIGS. 3A and 3B illustrate aspects of a device which can have a toroidal balloon stowed therein, where the balloon is illustrated in exemplary folding orientations.
Figure 4:
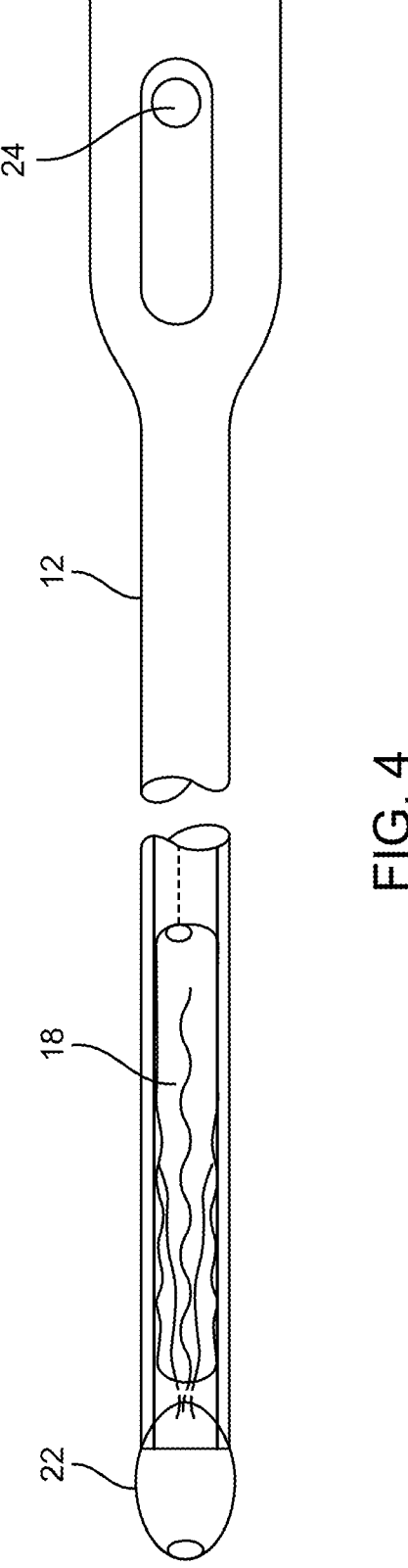
FIG. 4 illustrates aspects of a device having a toroidal balloon stowed therein.

FIGS. 3A and 4 illustrate a balloon 18 stowed within the device 10, for example within a lumen 17 of a distal end 16 of a shaft 12. As shown, the balloon 18 is stowed with tethers 32 generally symmetrically in two elongated sections such that the bulk and crossing profile of the balloon is minimized. The tethers 32 lay alongside the folded balloon 18 along with the support shaft 20. According to some embodiments, support shaft 20 includes a lumen 21 configured to receive a guidewire. In some cases, fluid can be provided through the support shaft 20 via the lumen 21 (or another separate lumen of the cap 22) which is in fluid communication with a corresponding lumen or lumens within the cap 22 which in turn provide fluid flow to the tether(s) 32. In this sense, shaft 20 may operate as a fill tube. As shown in FIG. 3A, when the cap 22 is retracted (e.g. proximally) against the distal end of the shaft 12, the cap 22 covers the distal edge 15 of the shaft 12, thereby providing a smooth atraumatic surface that can be safely maneuvered throughout the patient's vasculature or other internal anatomy. FIG. 3A also depicts a proximal tether 40 attached with the balloon 18. In some embodiments, the cap 22 can be provided as a manifold cap. In some cases, the cap 22 can be provided as a trunnion cap.

Figure 3B:
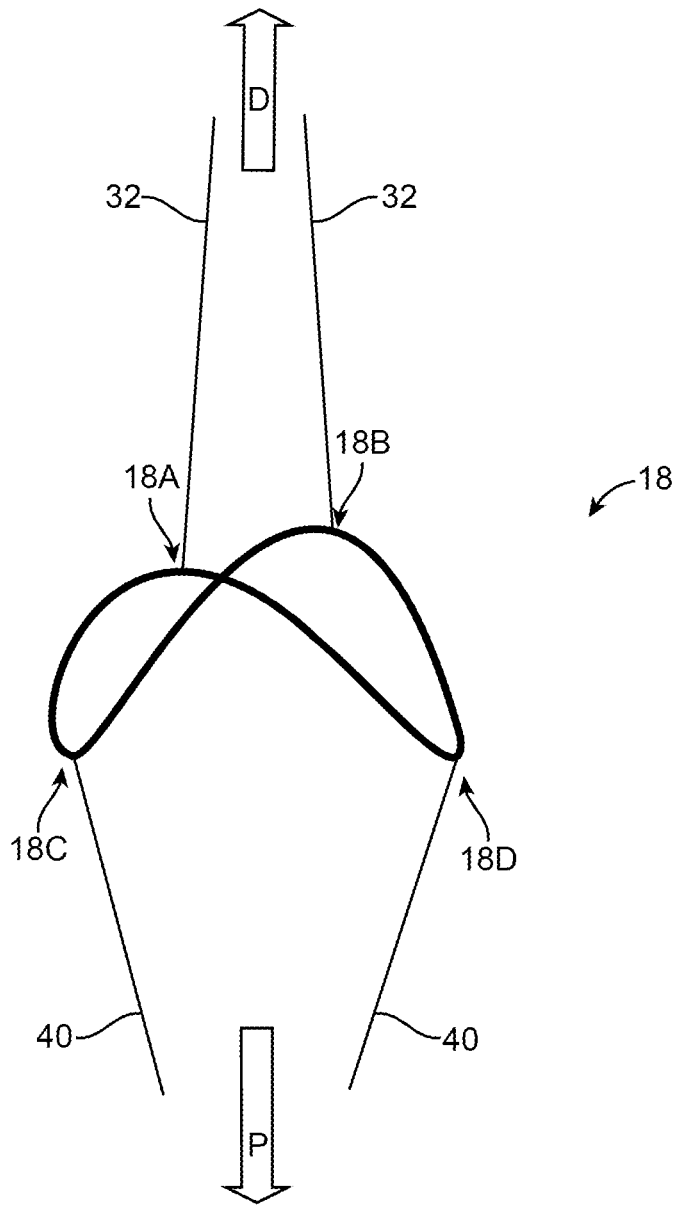

The schematic illustration of FIG. 3B provides additional details regarding the balloon folding process. As shown here, distal tethers 32 can draw two opposing points 18A and 18B of the balloon 18 in a distal direction (as indicated by arrow D), while tethers 40 can draw two opposing points 18C and 18D of the balloon 18 in a proximal direction (as indicated by arrow P). In this sense, a first distal attachment point at 18A can be diametrically opposed to a second distal attachment point at 18B. Similarly, a first proximal attachment point at 18C can be diametrically opposed to a second proximal attachment point at 18D. In some cases, one or more tethers 40 may remain stationary while one or more tethers 32 are drawn toward the D direction. In some cases, one or more tethers 32 may remain stationary while one or more tethers 40 are drawn toward the P direction. As shown here, when tethers are pulled, the balloon 18 can assume a configuration which can be referred to as a four eared ring, a wave ring, a sinusoidal or wave annulus (e.g. wrapped around a cylinder or similar object, with a frequency of two), and the like. The configuration can be considered to have two peaks (e.g. at points 18A and 18B) and two valleys (e.g. at points 18C and 18D). In this embodiment, pulling point 18A is 180° opposite to pulling point 18B on the balloon, and pulling point 18C is 180° opposite to pulling point 18D. This folding action can reduce the crossing profile of the balloon so that it may be able to pass through or be positioned within a relatively small opening. As further discussed elsewhere herein, the pulling action on one or more of the tethers can be performed in a staggered or sequenced fashion, which can result in a folded balloon having an even smaller crossing profile and/or a folded balloon with redistributed bulk properties. Such staggered or sequenced pulling of the tethers can ensure that junctions (between the tethers and the balloon) do not coincide along an axis, whereby the cumulative bulk of each junction could increase the crossing profile of the folded balloon.

Referring back to FIG. 2A, the device 10 can be advanced within the aorta A (e.g in the direction indicated by arrow ADV) until the stowed balloon 18 is positioned approximately within the target site. In some embodiments, the device 10 has radiopaque markers 25 to visualize position. The target site can be the aortic side branch ostium S leading to the organ for which occlusion is desired. As discussed further elsewhere herein, a balloon can also be filled with a fluid such as a radiopaque fluid.

Once position is obtained with fluoroscopic guidance, the balloon 18 is deployed from the catheter device distal end 16 by acting on the manipulator 24 (e.g. shown in FIG. 4). In particular, the balloon 18 is deployed by advancing the support shaft 20 (e.g. support shaft 20 shown in FIG. 1A) so that the tethers 32 pull the balloon 18 from the distal end 16 of the shaft 12. The tethers 32 when used as pairs can be positioned so as to lay in orthogonal planes which have an intersection about the toroidal balloon's major axis. With each pair connecting on opposite sides. This provides a statically determinate fixing of the compliant toroid balloon 18. A handle at the proximal end 14 can have fluid connectors for syringes to fill the tethered compliant toroidal balloon 18, and trigger features connected to the balloon tethers to provide actuation of deploying and stowing. In some embodiments, the cap 22 can be provided as a manifold cap. In some cases, the cap 22 can be provided as a trunnion cap.

Figure 5:
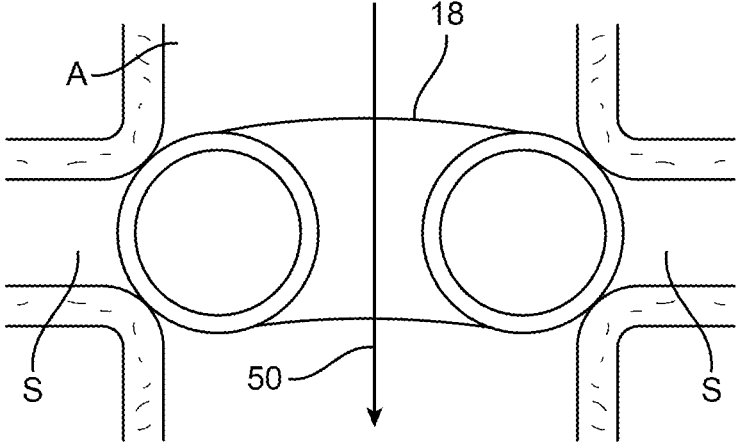
FIG. 5 is a cross-section view of an embodiment of the toroidal balloon inflated and sealing off one of the aortic vessel branches without aortic distension.

FIG. 5 is a schematic illustration of a cross-section of the inflated toroidal balloon 18 within the aorta A, wherein the balloon 18 occludes side branches S while allowing blood flow through the opening in the toroidal balloon 18 (as indicated by arrow 50). The tethered compliant toroidal balloon 18 can be filled by opening an inflation valve or using an automatic Luer valve, and connecting a syringe filled with saline (or any inflation fluid) and/or contrast medium so as to provide radiopacity which is used for cine fluoroscopy. Once the desired inflation level for the balloon 18 is reached, the valve can be closed to secure the balloon's inflated pressure. Additionally, a lumen providing fluid communication from the handle to the catheter distal end 16 can provide a means to introduce distal contrast media to assist with balloon position while being inflated ascertaining security of occlusion, and occlusion interference functionality.

A significant benefit for the patient is to provide a seal to occlude the side branches S using pressure only necessary to position the tethered compliant toroidal balloon 18 over the target aortic ostium as opposed to using pressure necessary to distend the aorta to archive anchoring, halting migration against the smooth lubricious inner lining of the aorta. A secondary benefit is allowing blood flow to the rest of the body including the symmetric organ which reduces the procedural rush having no concerns over infarction caused by the occlusion device.

Figure 6:
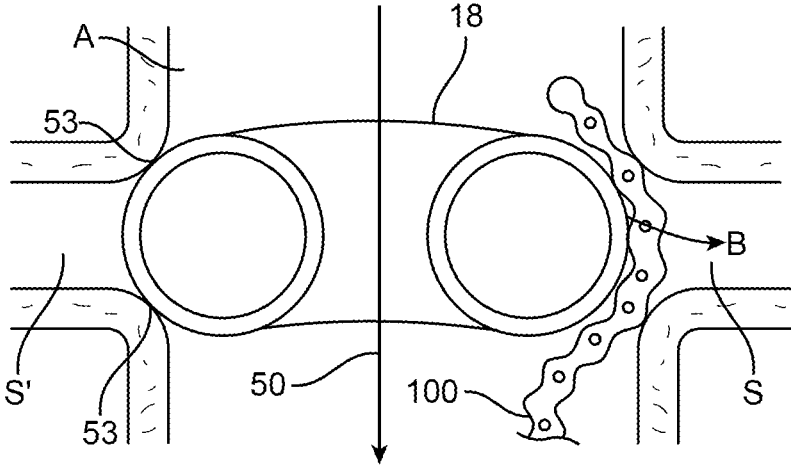
FIG. 6 illustrates an embodiment of the toroidal balloon inflated and sealing off an aortic side branch while an occlusion interference device allows perfusion to the opposite aortic side branch.

Since artery side branches S typically occur in pairs and anatomically tend to exist at the same axial position in the aorta A, an occlusion interference device 100 or "seal breaker" could be incorporated into (or used in conjunction with) the device 10 to allow blood perfusion into one of the side branches while the other side branch is occluded. FIG. 6 is a schematic illustration of a cross-section of the inflated toroidal balloon 18 within the aorta A, wherein an interference device 100 is placed over the side branch S so that the balloon 18 occludes side branch S' while allowing blood flow through the opening in the toroidal balloon 18 (as indicated by arrow 50) and allowing blood flow into side branch S. In this embodiment, the occlusion interference device 100 comprises a tube having scallops in the wall of the tube providing fluid communication about the sides, and center thus allowing the circulation to enter the desired side branch ostium (e.g. from the aorta). In some embodiments, the occlusion interference device 100 has spline features which run axially long enough to go by the targeted aortic ostium and toroidal balloon 18 which is adjacent to the target ostium and aortic wall. The spline design can have patterns to include a plurality of flutes, such as ranging from 3 to 20, and in some cases approximately 5. Often, each flute will have surfaces that do not present traumatic edges. Each flute edge will have a radii, or non-uniformly placed scallops to present an atraumatic surface. The occlusion interference device 100 may be stowed proximal to the stowed tethered compliant toroidal balloon and may have a distally curving axial jog predisposed to positioning occlusion interference features adjacent to the aortic ostium. After the tethered compliant balloon is deployed, the occlusion interference device "seal breaker" 100 can be deployed before balloon inflation. Radiopaque markers can help guidance with fluoroscopy during tethered compliant balloon inflation. As shown in FIG. 6, there are two side branch vessels S' and S located opposite one another, and side branch S' is in contact with the balloon 18 whereas the side branch S is not in contact with the balloon 18, due to the presence of the intervening seal breaker or interference device 100. Hence, blood does not flow into side branch S' from the aorta A, whereas blood does flow into side branch S from the aorta, as indicated by arrow B. The interference device 100 operates to prevent full occlusion of the side branch S, while side branch S' is occluded by the balloon 18, e.g. at locations 53 (which can form a sealing ring about the proximal or medial portion of the side branch).

The occlusion interference device 100 can be stowed in the device 10 for the optional deployment over one of the side branches as opposed to occluding the pair of ostia typically located at the same axial position in the anatomy.

At the conclusion of the procedure, stowing action is performed after the inflation valve is opened, and the tethered compliant toroidal balloon 18 is fully deflated by aspirating the fill syringe which can collapse the tethered compliant toroidal balloon. If an occlusion interference device 100 is used, the device 100 can then be pulled back in along with the distal contrast delivery lumen.

Figure 7A:
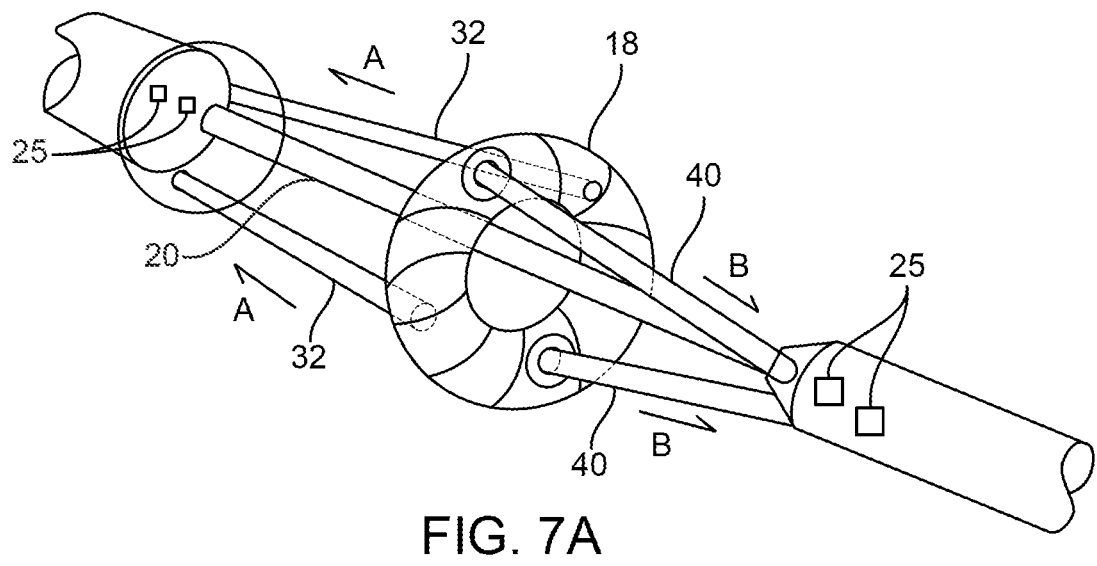
FIGS. 7A to 7H depict aspects of toroidal balloon devices and methods, according to embodiments of the present invention.
Figure 7B:
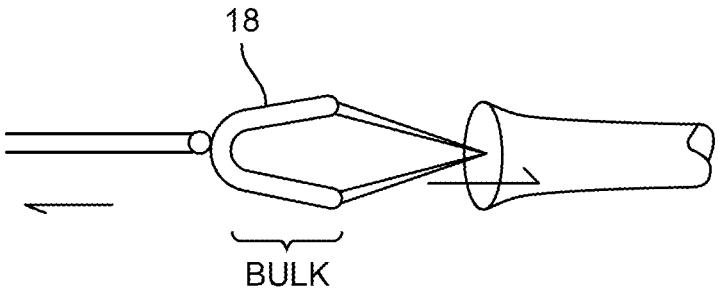
Figure 7C:
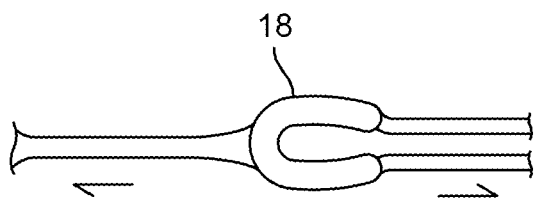
Figure 7D:
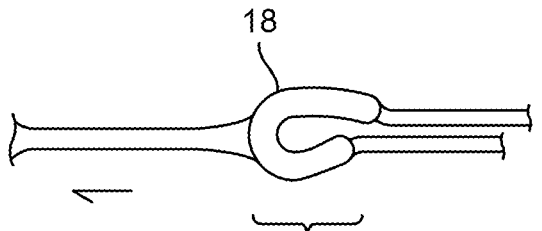

Stowing may also involve pulling on both tether pairs in opposite directions along the toroid major axis. For example, as shown in FIG. 7A, tethers 32 can be pulled in the direction indicated by arrows A (e.g. distally) and tethers 40 can be pulled in the direction indicated by arrows B (e.g. proximally) This can fold the compliant toroid balloon into four (4) sections and create a relatively greater packing bulk and associated larger profile, as depicted in FIGS. 7B and 7C. In contrast, in some embodiments, it is possible to pull on one of the inflation tethers 40 thus collapsing the compliant toroid balloon 18 into two sections with less bulk achieving a lower profile device, as depicted in FIG. 7D. The offset can reduce the stowed bulk of the balloon. The manipulator 24 can be designed accordingly to create this action of pulling on one inflation tether 40, and allow slack on the aforementioned element while pulling the compliant toroid balloon 18 out from the stowed position with the distal tethers. Hence, the pulling action on the tethers can be staggered, by pulling on one tether first, and then pulling on another tether, and this staggered pulling action can be accomplished by using a mechanism with a locking function that provides offset pulling (e.g. so that the folded balloon can be stowed within a small space). When the tethered compliant toroidal balloon is withdrawn back into the catheter distal end 16, the cap 22 then closes off the end 16 once again providing a smooth faired atraumatic surface and the device 10 is withdrawn from the body through the cannulation site followed by a femoral closure procedure. In some embodiments, a device can have one or more radiopaque markers 25 to visualize position.

Another embodiment eliminates the use of distal end 16 and shaft 12 and can simply have the toroidal balloon connect to and be in fluid communication with shaft 20 transferring inflation pressure to toroidal balloon patent tethers 32 and 40.

As discussed elsewhere herein, the balloon 18 can be stowed with tethers 32 generally symmetrically in two elongated sections such that the bulk and crossing profile is minimized. The crossing profile can refer to the diameter or cross-section of the balloon when collapsed or stowed. Minimizing the crossing profile allows the balloon to be passed through a small hole or aperture, for example when the device is advanced into or retracted from the patient's body. As such, a reduced crossing profile enables the device to be used more easily to obtain access to a treatment site within a patient. Upon deployment, the struts or tethers can be even in length to allow the plane of the balloon to be perpendicular to the axis of the vessel. To stow and/or collapse and remove the balloon, one of the proximal tethered struts can have the ability to shorten. The tethered strut can be shortened either passively, or by physician actuation. This can cause a lead portion of the balloon to fold down thus distributing the bulk of the balloon and attain a small crossing profile.

Some embodiments can implement a staggering of the tethers during balloon retraction, which can orient the bulk distribution reducing the crossing profile of the balloon, for example as shown in FIG. 7D. The catheter can have a mechanism that pulls on one of the proximal tethers (leading tethers when retracting) to offset the balloon bulk. This can help to ensure that the tether does not get sucked down or aspirated.

Figure 7E:
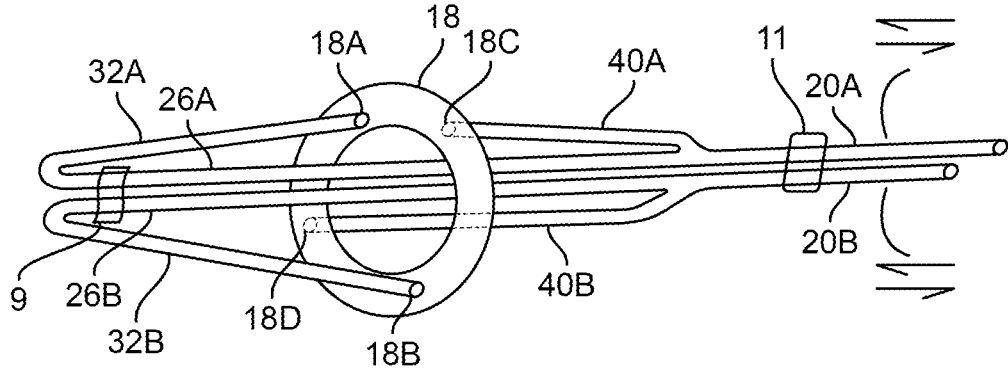

FIG. 7E depicts a configuration of a device in a deployed configuration, where balloon 18 is inflated, and coupled with first distal tether 32A at first distal attachment point or junction 18A, with second distal tether 32B at second distal attachment point or junction 18B, with first proximal tether 40A at first proximal attachment point or junction 18C, and with second proximal tether 40B at second proximal attachment point or junction 18D. In this configuration, distal attachment points or junctions 18A and 18B are in a distal fore-aft plane and proximal attachment points or junctions 18C and 18D are in a proximal fore-aft plane. Fluid can be delivered to and/or removed from balloon 18 via fluid flow through first support shaft 20A which is in fluid communication with first distal tether 32A (e.g. via first bridge shaft 26A) and first proximal tether 40A, and/or via fluid flow through second support shaft 20B which is in fluid communication with second distal tether 32B (e.g. via second bridge shaft 26B) and second proximal tether 40B. The device can also include a distal guide 9 that is coupled with first bridge shaft 26A and second bridge shaft 26B, and/or a proximal guide 11 that is coupled with first support shaft 20A and second support shaft 20B.

Figure 7F:
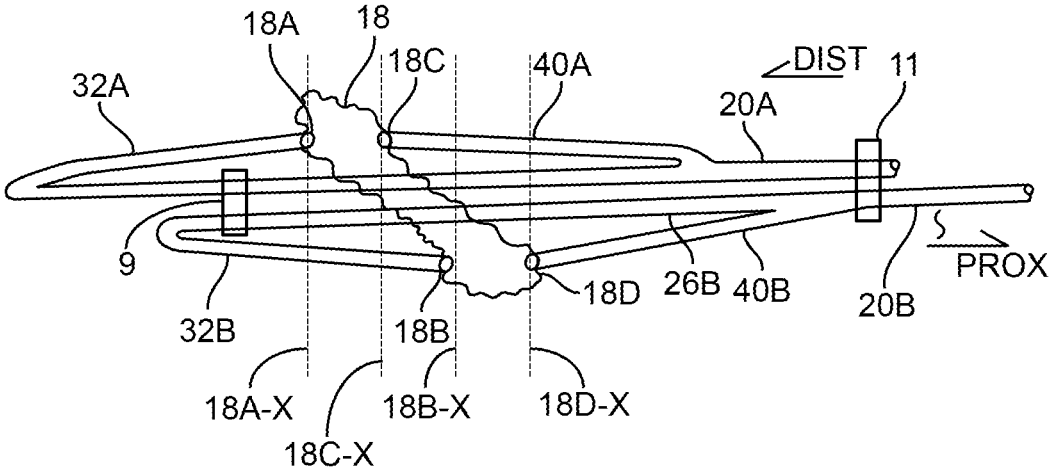
Figure 7G:
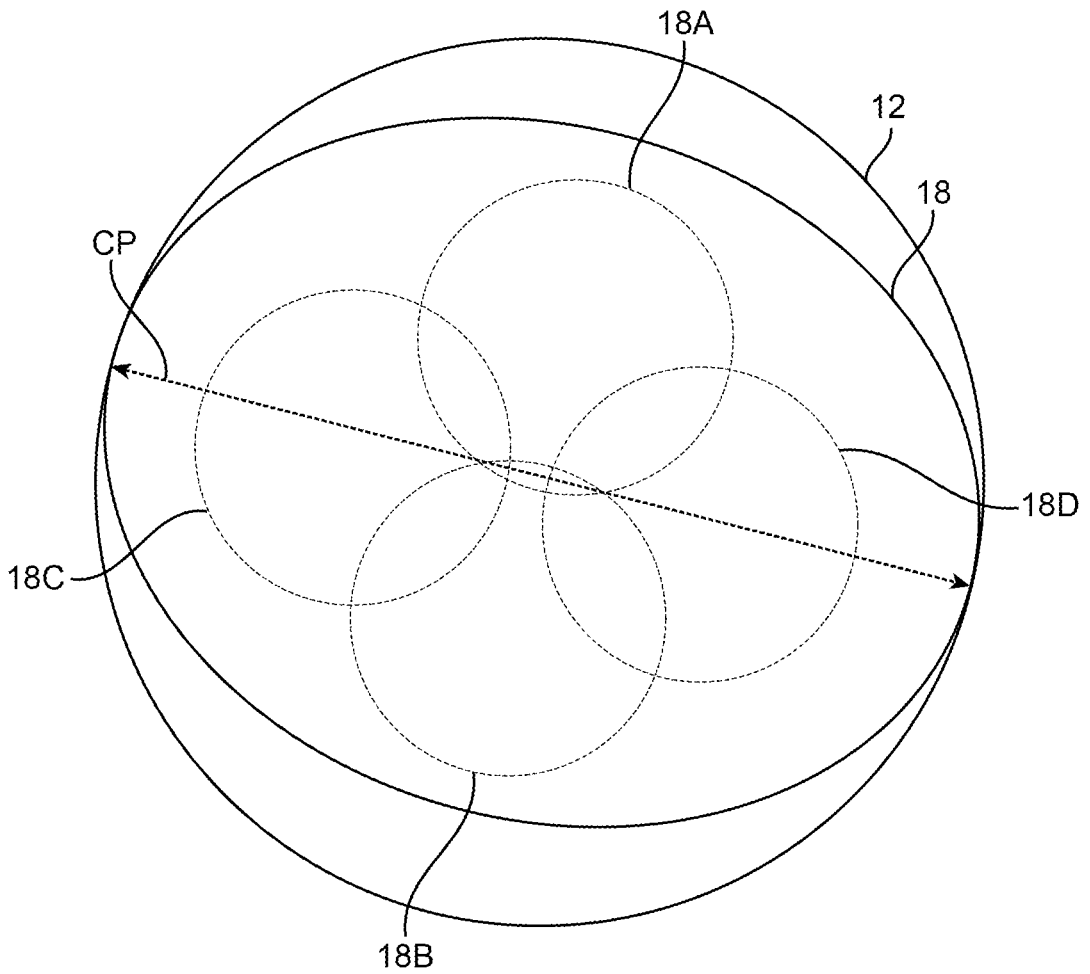

FIG. 7F depicts a configuration of a device in a stowed (or stowable) configuration, where balloon 18 is deflated, and coupled with first distal tether 32A at first distal attachment point or junction 18A, with second distal tether 32B at second distal attachment point or junction 18B, with first proximal tether 40A at first proximal attachment point or junction 18C, and with second proximal tether 40B at second proximal attachment point or junction 18D. In this configuration, the distal attachment point or junction 18A, the second distal attachment point or junction 18B, the first proximal attachment point or junction 18C, and the second proximal attachment point or junction 18D are each in a different or staggered location along the fore-aft axis of the device (e.g. locations 18A-X, 18B-X, 18C-X, and 18D-X, respectively). This can be achieved by moving the first support shaft 20A in one direction (e.g. as indicated by arrow DIST), and/or moving the second support shaft 20B in an opposing direction (e.g. as indicated by arrow PROX). This can help to assure that each of the balloon-tether attachment points or junctions do not occur in the same fore-aft plane, thus reducing the crossing profile of the balloon-tether combination. FIG. 7G provides an end view of such a configuration, where there is overlap between each of the junctions 18A, 18B, 18C, 18D, thus providing a reduced crossing-profile CP within an elongate shaft 12.

Figure 7H:
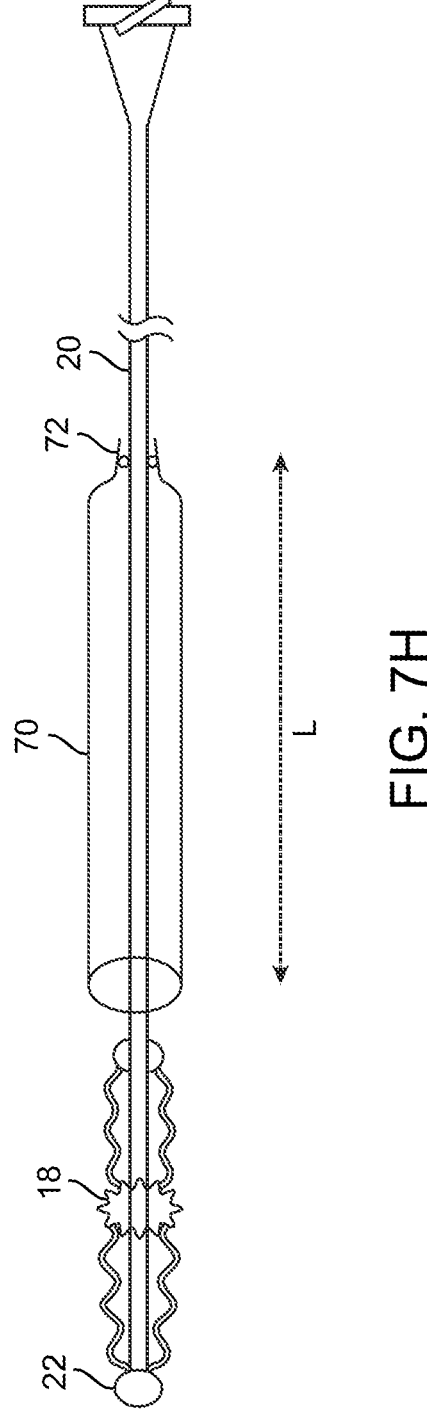

As shown in the cross-section view of FIG. 7H, a device can include a short or adjunct introducer 70 having a proximal seal 72 that can create a seal with a support shaft 20. In some cases, a length L of the introducer 70 can have a value of about 3 cm. The introducer 70 can operate to help reduce the crossing profile of the device, for example by only being used for insert/removal and not with a sheath introduced in the patient's body. According to some embodiments, by not having a short introducer put into the body (e.g. remaining with the device), the crossing profile can be reduced by the wall thickness of the sheath.

Figure 8:
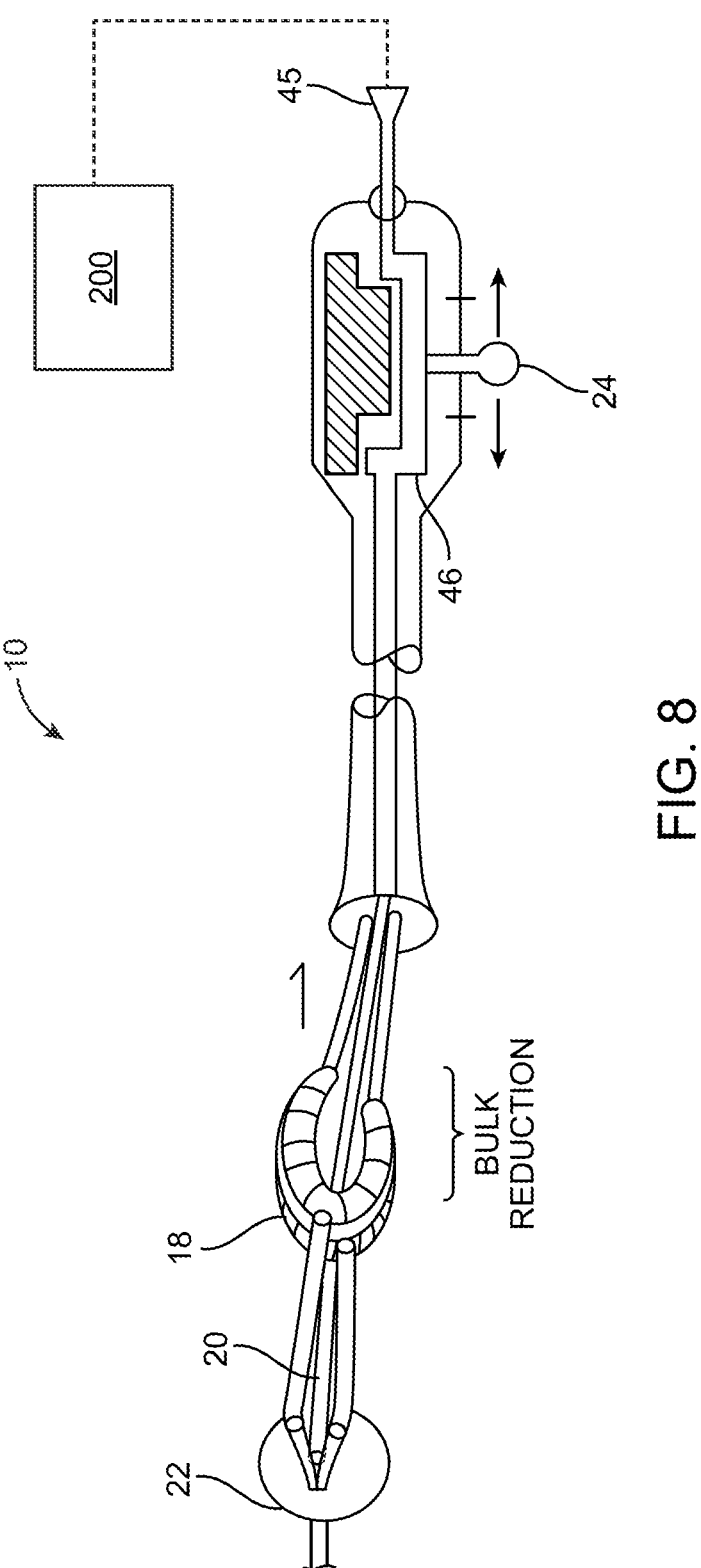
FIG. 8 depicts aspects of a toroidal balloon device, according to embodiments of the present invention.

FIG. 8 depicts additional aspects of a manipulator handle 24, which can be used to assist in the folding and/or retraction of the balloon 18. Bulk reduction in the balloon can be achieved by staggering the drawings action on the balloon attachments points, as the balloon is folded and/or being drawn into the catheter. Relatedly, in instances where the device is configured to provide staggered drawings actions, the tethers can run the full length of the catheter. Further, one of the lumens can go proximal all the way to the manipulator to pull on first when the toroidal balloon is drawn down. This can necessitate more fluid communication channels for the remaining tube tethers. In some instances, at the location where a tether meets or is coupled with the balloon, there is a bulk spot or junction. In some cases, the manipulator handle 24 can provide fluid communication between a Luer connector 45 and a cap or ball tip via a support shaft or fluid passage 46. In some embodiments, the cap 22 can be provided as a manifold cap. In some cases, the cap 22 can be provided as a trunnion cap. As shown here, the device 10 can include or be in communication with a fluid assembly 200, which may be a fluid source or container. The fluid assembly 200 can be configured to provide any of a variety of fluids for the balloon 18, and/or to receive any of a variety of fluids therefrom. Exemplary types of fluids are discussed elsewhere herein, and can include, for example, saline, contrast media, air, gas, liquid, or the like. Additional aspects of a manipulator are discussed elsewhere herein, for example with reference to FIG. 11.

Figure 9:
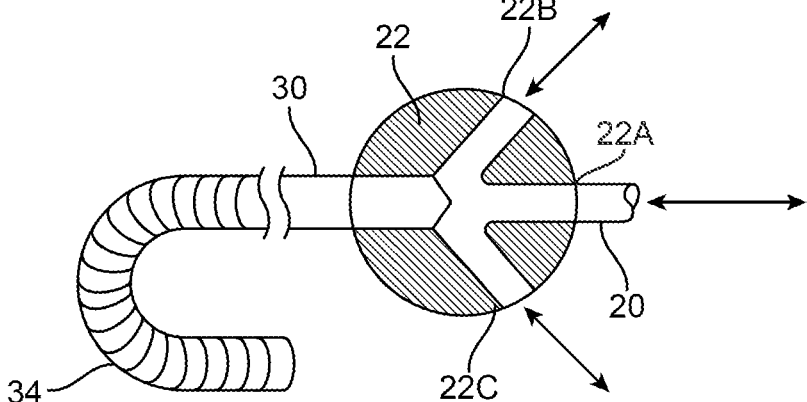
FIG. 9 depicts aspects of a toroidal balloon device, according to embodiments of the present invention.

As discussed elsewhere herein, a cap can operate as a manifold. FIG. 9 provides a cross-section view of a cap 22, having a proximal port 22A which can be in fluid communication with a support shaft 20, a first lateral port 22B which can be in fluid communication with a first fluidic tether (not shown), a second lateral port 22C which can be in fluid communication with a second fluidic tether (not shown). The proximal port 22A, first lateral port 22B, and second lateral port 22C can all be in fluid communication with each other. Hence, in some embodiments, the tethers (e.g. 32 in FIG. 7A) can be inflatable, and the cap or ball tip 22 can operate as a manifold. In this sense, fluid can be provided to the balloon 18 via one or more tethers 32, which in turn receive fluid via the cap 22, which in turn can receive fluid from the shaft 20. With regard to fluid flow in the opposite direction, fluid may flow from balloon 18 through one or more tethers 32 to the cap 22, and from the cap 22 into the shaft 20. As shown here, a guidewire 30 having a floppy distal tip 34 can extend from or be coupled with the cap 22.

Figure 10:
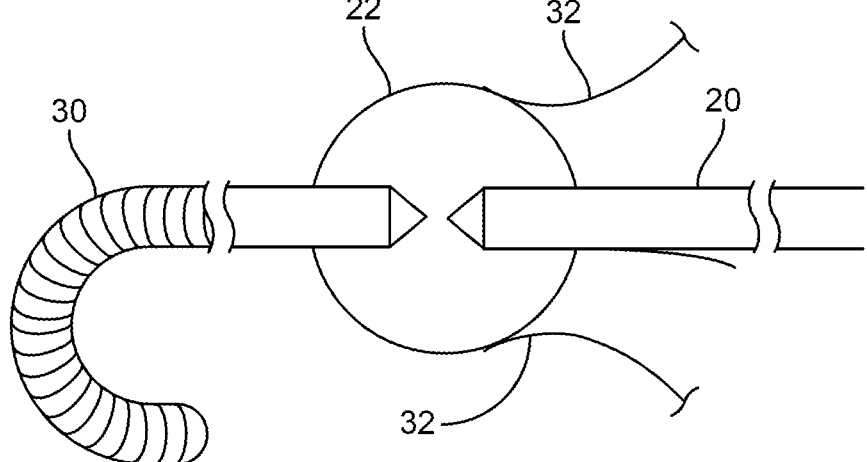
FIG. 10 depicts aspects of a toroidal balloon device, according to embodiments of the present invention.

As shown in FIG. 10, in some cases, the shaft 20 may not provide fluid to the balloon via tether(s) 32 and cap 22 and the shaft 20 can be provided as a solid element with no internal lumen or fluid passageway. In this sense, cap 22 may operate as a trunnion.

In some embodiments, an auxiliary tether can run the length of the catheter from the manipulator (handle) down to one of the proximal tethers, for example about mid length of the tether, which can be pulled upon after deflation to stagger the stowed bulk ends of the balloon facilitating retrieval into the cannulation. This approach can be particularly useful in folding up and/or stowing the balloon, allowing it to be passed through a small aperture.

Figure 11:
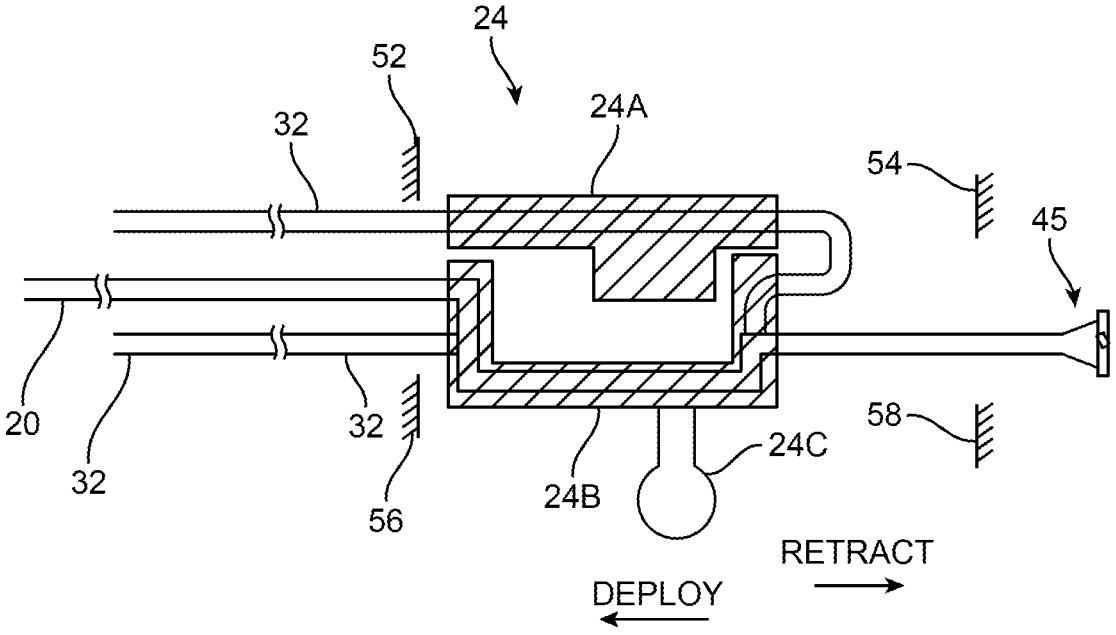
FIG. 11 depicts aspects of a toroidal balloon device, according to embodiments of the present invention.

As illustrated in FIG. 11, a manipulator handle 24 can provide fluid communication to multiple catheter and/or tether components, and can also assist with retraction of the balloon so as to reduce the crossing profile of the balloon. For example, the manipulator handle 24 can provide fluid communication between the Luer connector 45 and a cap or ball tip via a support shaft 20. The manipulator handle 24 can provide fluid communication between the Luer connector 45 and a cap or ball tip via a one or more inflation tethers 32. As shown here, a manipulator handle 24 can include a first portion 24A that can move between end travel stops 52 and 54, and a second portion 24B that can move between end travel stops 56 and 58. In some cases, a manipulator handle 24 can include a knob 24C in operative association with second portion 24B. As shown here, first portion 24A can be deployed or advanced in a distal direction until it reaches stop 52 and retracted in a proximal direction until it reaches stop 54. Similarly, second portion 24B can be deployed or advanced in a distal direction until it reaches stop 56 and retracted in a proximal direction until it reaches stop 58. In some cases, a device can include a locking stabilizer, although that is optional. A locking mechanism or stabilizer can include a ball bearing in a track that can operate to lock-out an adjacent sliding component.

Figures 1, 12A:
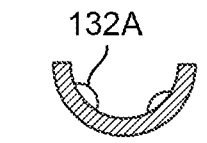
FIGS. 12A, 12A-1, 12A-2, 12A-3, and 12B depict aspects of toroidal balloon devices and methods, according to embodiments of the present invention.
Figures 2, 12A:
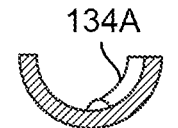
Figures 3, 12A:
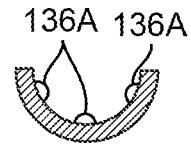
Figure 12A:
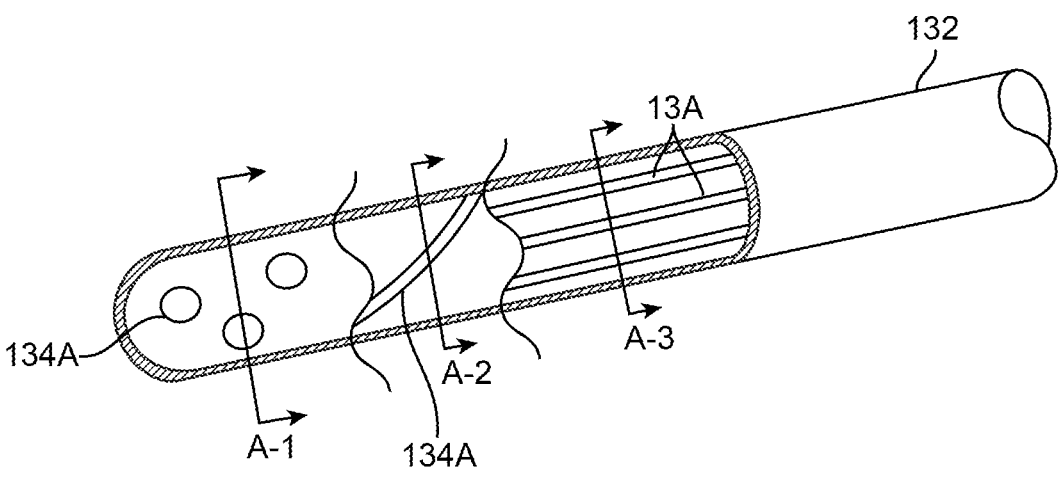
Figure 12B:
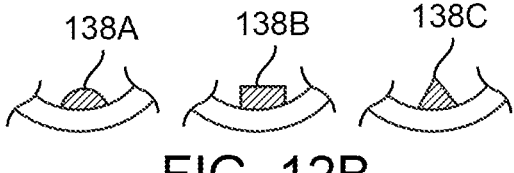

FIG. 12A provides a cut-away view depicting an exemplary tether 132 having a variety of internal surface geometry features. For example, the cross-section corresponding to section A-1 shown in FIG. 12A-1 includes raised splines or spots 132A, which can be round, square, triangular, or any desired shape. The cross-section corresponding to section A-2 shown in FIG. 12A-2 includes a raised helix or screw thread 134A, which can be round, square, triangular, or any desired shape. The cross-section corresponding to section A-3 shown in FIG. 12A-3 includes a plurality or raised ribs 136A. As shown in FIG. 12B, raised ribs can have a cross-section profile that is rounded (138A), square or rectangular (138B), triangular (138C), or the any desired shape.

In some cases, there may be a mechanism such as a coarse thread that is disposed within an inflation tether, thus preventing or inhibiting the tether from collapsing or sealing. In some cases, embodiments of the present invention encompass devices which include inflation tethers having one or more internal surface geometry features that prevent a tether from collapsing when suction is applied thereto. In some cases, an internal surface geometry feature can include one or more raised helical spines. The internal surface geometry feature can also be one or more raised bumps. The internal surface geometry feature can include splined beading. A spline can have one or more lobes which are prismatic or round in cross-section. Beading can include a loose braid or a twisted string.

In some instances, an internal element (e.g. thread) may have a helical winding of fibers, so that when the internal element is compressed, it can still prevent sealing of the tether tube due to the presence of internal open spaces within the compressed internal element. As noted elsewhere herein, in some instances an internal element can be integral with or coupled to the interior of the tether. In some instances, the internal element is provided as an element separate from the tether. Where internal element contains multiple helices, the helices can be oriented in non-parallel configurations, so there will be little or no intermeshing when the internal element is compressed.

There is a possibility that aspiration of fluid from the inflated balloon can be choked off from the molded tubing tethers which provide fluid communication collapsing when suction is applied. This could potentially compromise the efficiency of the stowing the balloon which is important to get the device out of the body through the cannulation port. To address this, it is possible to implement surface geometry features inside the molded tube wall which interfere with the internal tubing wall sealing if the tube walls do come in into contact from internal pressure being lower than external pressure.

Such internal surface geometry features can be created by a mold mandrel which has a helical groove to produce a raised helical spline inside the tube wall which would inhibit the internal walls from sealing. The features can also be raised bumps that are irregularly shaped and spaced to not allow sealing if the tube was drawn down. These feature like the helix can be produced by adding to the mold mandrels. In some embodiments, a raised helical spline can be a single continuous spline running the length of the tether. This spline can interfere with sealing or shutting off the aspiration flow of the collapsed tether. Spline features and similar surface geometry features can be a mold mandrel which has a helical groove to produce a raised helical spline inside the tube wall which would inhibit the internal walls from sealing.

Additional techniques can be used to stop or inhibit the tube tethers from sealing. For example, interfering structures can be added such as a splined beading placed inside as a separate component. The spline could have 2, 3, or more lobes which are prismatic or round in cross-section. The beading can employ shapes which inhibit the sealing of collapsed tube walls. The beading can be a loose braid or twist string type material.

The preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All features of the described systems and devices are applicable to the described methods mutatis mutandis, and vice versa. Embodiments of the present invention encompass kits having toroidal occlusion balloon systems and devices as disclosed herein. In some embodiments, the kit includes one or more toroidal occlusion balloon systems or devices, along with instructions for using the system or device for example according to any of the methods disclosed herein.

Although the foregoing invention has been described in some detail by way of illustration and example for purposes of clarity of understanding, one of skill in the art will appreciate that certain changes, modifications, alternate constructions, and/or equivalents may be practiced or employed as desired, and within the scope of the appended claims. In addition, each reference provided herein is incorporated by reference in its entirety to the same extent as if each reference were individually incorporated by reference. Relatedly, all publications, patents, patent applications, journal articles, books, technical references, and the like mentioned in this specification are herein incorporated by reference to the same extent as if each individual publication, patent, patent application, journal article, book, technical reference, or the like was specifically and individually indicated to be incorporated by reference.

What is claimed is:

1. A method of sealing an aortic side branch in an aorta of a patient using an occlusion device, comprising:
    advancing the occlusion device within the aorta of the patient, the occlusion device having a toroidal balloon;
    positioning the toroidal balloon of the occlusion device adjacent to the aortic side branch of the patient; and
    inflating the toroidal balloon so that a side surface of the toroidal balloon prevents peripheral blood flow from the aorta into the aortic side branch while a central aperture of the toroidal balloon allows descending aortic blood flow therethrough,
    wherein the occlusion device comprises a distal tether assembly coupled with the toroidal balloon, and the step of inflating the toroidal balloon comprises delivering fluid in a proximal direction through the distal tether assembly into the toroidal balloon.

2. The method according to claim 1, wherein the aortic side branch comprises a member selected from the group consisting of a mesenteric artery side branch, a renal artery side branch, a gonadal artery side branch, a celiac artery side branch, and an intercostal artery side branch.

3. The method according to claim 1, wherein the aortic side branch is located in a descending portion of the aorta of the patient.

4. The method according to claim 1, wherein the aortic side branch is located in an abdominal portion of the aorta of the patient.

5. The method according to claim 1, wherein the occlusion device further comprises a manifold cap coupled with the distal tether assembly, and the step of inflating the toroidal balloon further comprises delivering fluid through the manifold cap into the distal tether assembly.

6. The method according to claim 5, wherein the occlusion device further comprises a support shaft coupled with the manifold cap, and the step of inflating the toroidal balloon further comprises delivering fluid in a distal direction through the support shaft into the manifold cap.

7. The method according to claim 1, wherein the occlusion device further comprises a guidewire, and the step of advancing the occlusion device within the aorta of the patient further comprises advancing the toroidal balloon along the guidewire.

8. The method according to claim 1,
    wherein the occlusion device further comprises an elongate shaft, a proximal tether assembly having a first proximal tether and a second proximal tether, and the distal tether assembly having a first distal tether and a second distal tether,
    wherein the first proximal tether is attached with the toroidal balloon at a first proximal attachment point and the second proximal tether is attached with the toroidal balloon at a second proximal attachment point opposite the first proximal attachment point,
    wherein the first distal tether is attached with the toroidal balloon at a first distal attachment point and the second distal tether is attached with the toroidal balloon at a second distal attachment point opposite the first distal attachment point, and
    wherein the method further comprises drawing the first distal attachment point and the second distal attachment point in a distal direction using the distal tether assembly or drawing the first proximal attachment point and the second proximal attachment point in a proximal direction using the proximal tether assembly so as to produce a four eared ring configuration in the toroidal balloon, and positioning the toroidal balloon within the elongate shaft when the toroidal balloon is in the four eared ring configuration.

9. A method of sealing an aortic side branch in an aorta of a patient using an occlusion device, comprising:

advancing the occlusion device within the aorta of the patient, the occlusion device having a toroidal balloon;

positioning the toroidal balloon of the occlusion device adjacent to the aortic side branch of the patient; and inflating the toroidal balloon so that a side surface of the toroidal balloon prevents peripheral blood flow from the aorta into the aortic side branch while a central aperture of the toroidal balloon allows descending aortic blood flow therethrough wherein the occlusion device further comprises an elongate shaft, a proximal tether assembly having a first proximal tether and a second proximal tether, and a distal tether assembly having a first distal tether and a second distal tether, wherein the first proximal tether is attached with the toroidal balloon at a first proximal attachment point and the second proximal tether is attached with the toroidal balloon at a second proximal attachment point opposite the first proximal attachment point, wherein the first distal tether is attached with the toroidal balloon at a first distal attachment point and the second distal tether is attached with the toroidal balloon at a second distal attachment point opposite the first distal attachment point, and wherein the method further comprises drawing the first distal attachment point and the second distal attachment point in a distal direction using the distal tether assembly or drawing the first proximal attachment point and the second proximal attachment point in a proximal direction using the proximal tether assembly so as to produce a four eared ring configuration in the toroidal balloon, and positioning the toroidal balloon within the elongate shaft when the toroidal balloon is in the four eared ring configuration.

10. The method according to claim 9, wherein the aortic side branch comprises a member selected from the group consisting of a mesenteric artery side branch, a renal artery side branch, a gonadal artery side branch, a celiac artery side branch, and an intercostal artery side branch.

11. The method according to claim 9, wherein the aortic side branch is located in a descending portion of the aorta of the patient.

12. The method according to claim 9, wherein the aortic side branch is located in an abdominal portion of the aorta of the patient.

13. The method according to claim 9, wherein the occlusion device comprises a proximal tether assembly coupled with the toroidal balloon, and the step of inflating the toroidal balloon comprises delivering fluid through the proximal tether assembly into the toroidal balloon.

14. The method according to claim 9, wherein the occlusion device further comprises a manifold cap coupled with the distal tether assembly, and the step of inflating the toroidal balloon further comprises delivering fluid through the manifold cap into the distal tether assembly.

15. The method according to claim 14, wherein the occlusion device further comprises a support shaft coupled with the manifold cap, and the step of inflating the toroidal balloon further comprises delivering fluid in a distal direction through the support shaft into the manifold cap.

16. The method according to claim 9, wherein the occlusion device further comprises a guidewire, and the step of advancing the occlusion device within the aorta of the patient further comprises advancing the toroidal balloon along the guidewire.

* * * * *